United States Patent
Kataoka et al.

(10) Patent No.: US 6,867,232 B1
(45) Date of Patent: Mar. 15, 2005

(54) GEL-LIKE RESIN MOLDED ARTICLE CONTAINED IN VOLATILIZATION CONTROL CONTAINER

(75) Inventors: Hironori Kataoka, Ikoma-gun (JP); Satoshi Hiratsuna, Kyoto (JP)

(73) Assignee: Dai-Ichi Kogyo Seiaku Co., Ltd., Kyoto (JP)

( * ) Notice: Subject to any disclaimer, the term of this patent is extended or adjusted under 35 U.S.C. 154(b) by 532 days.

(21) Appl. No.: 09/692,334

(22) Filed: Oct. 19, 2000

(30) Foreign Application Priority Data

Oct. 20, 1999 (JP) .......................................... 11-298325

(51) Int. Cl.[7] .............................................. A01N 47/46
(52) U.S. Cl. ...................... 514/514; 514/918; 514/919; 514/920; 523/122; 424/405; 424/406; 424/411
(58) Field of Search .............................. 514/514, 235.5, 514/919; 424/402, 76.3, 642, 405, 406, 409, 411

(56) References Cited

U.S. PATENT DOCUMENTS

| | | | |
|---|---|---|---|
| 5,645,845 A | * | 7/1997 | Neumann et al. ........... 424/402 |
| 5,880,150 A | | 3/1999 | Fujita et al. ................. 514/514 |
| 5,928,661 A | | 7/1999 | Fujita et al. ................. 424/402 |
| 5,968,498 A | | 10/1999 | Okada et al. ............... 424/76.3 |

FOREIGN PATENT DOCUMENTS

| | | |
|---|---|---|
| JP | 09-151317 | 6/1997 |
| JP | 11222279 | 8/1999 |
| JP | 11239608 | 9/1999 |

* cited by examiner

*Primary Examiner*—Neil S. Levy
(74) *Attorney, Agent, or Firm*—Marshall, Gerstein & Borun LLP

(57) ABSTRACT

A gel-like resin molded article contained in a volatilization control container is provided. A gelled drug containing allyl isothiocyanate and a resin base is contained in a container, and the container is provided with an opening portion which occupies a contact area between the gelled drug and air in the proportion of 0.01 to 50%. Alternatively, the container is made of a thermoplastic resin film whose permeability to allyl isothiocyanate is from 0.05 to 10 mg/cm² day. The molded article controls the volatilization rate and volatilization time period of allyl isothiocyanate by gelling allyl isothiocyanate.

11 Claims, 2 Drawing Sheets

GEL-LIKE RESIN MOLDED ARTICLE CONTAINED IN VOLATILIZATION CONTROL CONTAINER

FIELD OF THE INVENTION

The present invention relates to a gel-like resin molded article contained in a volatilization control container and, more particularly, to a gel-like resin molded article contained in a volatilization control container, and containing allyl isothiocyanate as an active ingredient, which exerts a repellant effect on noxious organisms for extended periods of time.

PRIOR ART

Allyl isothiocyanate has been known as a principal ingredient of Japanese horseradish, and various applications have been suggested utilizing its stimulant action. For example, it has been suggested to use allyl isothiocyanate as an active ingredient in antimicrobial agents, antifungal agents, preservatives, and repellents for noxious organisms. However, allyl isothiocyanate cannot be used as is because of its comparatively high volatility. Accordingly, it is necessary to control the volatilization rate of allyl isothiocyanate during use, and to set the duration for allyl isothiocyanate volatilization to meet the needs of a particular end use.

In view of the above points, a resin molded article is disclosed in Japanese Patent Publication No. Hei 9-151317 (A). This molded article can contain a large amount of allyl isothiocyanate, such that some degree of product durability can be expected.

However, because the molded article is a rigid cured article, allyl isothiocyanate contained in the interior of the molded article cannot migrate to the surface of the object after allyl isothiocyanate in the vicinity of the surface has volatilized over time. Therefore, the amount of allyl isothiocyanate that volatilizes is reduced after about one month at most, and the useful life of the article is not sufficient for repellent applications. In addition, the shape of the resulting molded article is difficult to deform, thus causing a handling problem during manufacture of the article.

To solve the problems described above, it is suggested to gel allyl isothiocyanate using a curable resin. Gelation makes it possible for the active ingredient to migrate to the surface of the molded article over time, and handling is improved.

However, because a gelled molded article described above contains a comparatively large amount of a volatile compound, the volatilization rate of the compound can be too great. Accordingly, it is necessary to control the volatilization rate of the allyl isothiocyanate by a method suitable to meet the needs of a particular end use.

The present invention addresses the problems described above, and, therefore, an aspect of the present invention is to provide a gel-like resin molded article contained in a container provided with a means for controlling the volatilization rate of allyl isothiocyanate.

SUMMARY OF THE INVENTION

The gel-like resin molded article contained in a volatilization control container according to the present invention comprises a gelled drug containing allyl isothiocyanate and a resin base, said gelled drug being contained in a container for controlling a volatilization rate of the allyl isothiocyanate, wherein the container comprises an opening portion, and said opening portion occupies a contact area between the gelled drug and air in a proportion of not less than 0.01% and not more than 50%.

By providing an opening portion that occupies a contact area between the gelled drug and air in the proportion of not less than 0.01% and not more than 50%, the volatilization rate of allyl isothiocyanate can be controlled, and the period of time for volatilization to meet the needs of a particular end use can be set.

The gel-like resin molded article contained in a volatilization control container according to the present invention comprises a gelled drug containing allyl isothiocyanate and a resin base, said gelled drug being contained in a container for controlling a volatilization rate of the allyl isothiocyanate, wherein the container comprises a thermoplastic resin film through which allyl isothiocyanate can permeate, and wherein permeability of the thermoplastic resin film to allyl isothiocyanate is not less than 0.05 mg/cm$^2$ day and not more than 10 mg/cm$^2$ day.

When the thermoplastic resin film of the container is a film having a permeability to allyl isothiocyanate of not less than 0.05 mg/cm$^2$ day and not more than 10 mg/cm$^2$ day, a volatilization time period desirable for a particular end use can be set by controlling the volatilization rate of allyl isothiocyanate.

Allyl isothiocyanate contained as a volatile drug in a gel-like resin molded article contained in a volatilization control container according to the present invention is known as a stimulant ingredient of Japanese horseradish. In the present invention, either natural or chemically synthesized allyl isothiocyanate can be used. The amount of allyl isothiocyanate is in a range of more than 20% by weight and not more than 85%, by weight, based on the total weight of the gelled drug. When the content of allyl isothiocyanate is not more than 20% by weight, the resulting gelled drug is hard, and the allyl isothiocyanate does not migrate from the interior to the surface of the gel, thereby undesirably shortening the useful time period for allyl isothiocyanate volatilization. On the other hand, when the content of allyl isothiocyanate is more than 85% by weight, it is difficult for the resulting gelled drug to maintain a gel-like form, resulting in poor handling, which also is undesirable.

In the molded article of the present invention, any resin base capable of serving as a gelling agent can be used as long as the resin can swell or dissolve in allyl isothiocyanate at normal temperature. Specific examples of resins include polyurethane resin, polyacrylamide, polystyrene, polyamide, polyacrylate, and copolymers of two or more monomers thereof. Among these resin bases, a polyurethane resin is preferred in view of the solubility and sustained release of allyl isothiocyanate from a polyurethane resin, as well as ease of manufacturing.

In the present invention, when using the polyurethane resin as the gel base, examples of a polyisocyanate as a starting material of the polyurethane include phenylene diisocyanate, tolylene diisocyanate, hexamethylene diisocyanate, diphenylmethane diisocyanate, naphthalene diisocyanate, xylylene diisocyanate, polymeric diphenylmethane diisocyanate, isophorone diisocyanate, and triphenylmethane diisocyanate, isocyanurate and biuret modifiers of such polyisocyanates, and diisocyanate prepolymers as adducts with polyols such as trimethylolpropane and hexanetriol. These polyisocyanates can be used alone or in combination. Among these polyisocyanates, hexamethylene diisocyanate and isophorone diisocyanate preferably are used because they do not cause yellowing as a result of light-induced reactions, which lowers the commercial value of articles.

Similarly, examples of a polyol as one of starting materials of the polyurethane resin include aliphatic polyols, such as trimethylolpropane, hexanetriol, ethylene glycol, propylene glycol, and hexanediol; aromatic polyols, such as xylylene glycol; polyhydric phenols, such as hydroquinone and catechol; condensates of these polyhydric alcohols and alkylene oxide; and polyol prepolymers, such as polyester polyol and polyether polyol. These polyols are used alone or in combination. Polyether polyols, such as castor oil, polyoxyalkylene polyol, and polytetramethylene ether glycol also can be used, as the polyol; as can polyester polyols, such as condensed polyester polyol, lactone polyester diol, and polycarbonate diol. These also are used alone or in combination. Among these polyols, castor oil is preferably used in view of its reactivity.

When using a polyurethane as the gel base, whether or not the resulting drug is in a gel-like form is related to on the types of polyisocyanate and polyol used as starting materials, as well as the ratio of the three ingredients, i.e., allyl isothiocyanate, polyisocyanate, and polyol. Table 1 shows the results obtained for tests designed to determine whether a good gel-like form is obtained by changing the weight ratio of the polyisocyanate (isocyanurate-type hexamethylene diisocyanate) and the polyol (glyceryl triricinoleate), wherein the amount of allyl isothiocyanate is held constant at 40%, by weight, based on the total weight of the gelled drug. Similarly, the test results in tests wherein the amount of allyl isothiocyanate is held constant at 60% and 80%, by weight, based on the total weigh of the gelled drug are shown in Table 2 and Table 3, respectively.

TABLE 1

| Allyl isothiocyanate | 40% by weight | | | | | | | | |
|---|---|---|---|---|---|---|---|---|---|
| Polyisocyanate % by wt., wt. ratio to polyol* | 53.91 (90) | 47.92 (80) | 41.93 (70) | 35.94 (60) | 29.95 (50) | 23.96 (40) | 17.97 (30) | 11.98 (20) | 5.99 (10) |
| Polyol. % by wt** wt. ratio to isocyanate | 5.99 (10) | 11.98 (20) | 17.97 (30) | 23.96 (40) | 29.95 (50) | 35.94 (60) | 41.93 (70) | 47.92 (80) | 53.91 (90) |
| Dibutyltin dilaurate | 0.1 | 0.1 | 0.1 | 0.1 | 0.1 | 0.1 | 0.1 | 0.1 | 0.1 |
| Solidified state | ○ | ○ | ○ | ○ | ○ | ○ | ○ | ○ | X |
| State after one day | good | good | good | good | good | good | good | good | — |
| Rubber hardness | 5–8 | 19–21 | 55–58 | 65–67 | 73–75 | 72–74 | 50–54 | 26–27 | — |

*Duranate THA-100 (isocyanurate type hexamethylene diisocyanate, manufactured by Asahi Chemical Industries Co., Ltd.)
**Castor oil (glyceryl triricinoleate)
Solidified state:
○: solidified into gel-like form within 24 hours
X: not solidified
State after one day:
Good: no change
Bleed: allyl isothiocyanate solution oozed out
Rubber hardness: measured value using Asker rubber hardness tester, Type C

TABLE 2

| Allyl isothiocyanate | 60% by weight | | | | | | | | |
|---|---|---|---|---|---|---|---|---|---|
| Polyisocyanate % by wt., wt. ratio to polyol* | 35.91 (90) | 31.92 (80) | 27.93 (70) | 23.94 (60) | 19.95 (50) | 15.96 (40) | 11.97 (30) | 7.98 (20) | 3.99 (10) |
| Polyol. % by wt** wt. ratio to isocyanate | 3.99 (10) | 7.98 (20) | 11.97 (30) | 15.96 (40) | 19.95 (50) | 23.94 (60) | 27.93 (70) | 31.92 (80) | 35.91 (90) |
| Dibutyltin dilaurate | 0.1 | 0.1 | 0.1 | 0.1 | 0.1 | 0.1 | 0.1 | 0.1 | 0.1 |
| Solidified state | ○ | ○ | ○ | ○ | ○ | ○ | ○ | ○ | X |
| State after one day | bleed | bleed | good | good | good | good | good | good | — |
| Rubber hardness | — | — | 48–49 | 53–55 | 58–61 | 64–67 | 45–58 | 22–25 | — |

*Duranate THA-100 (isocyanurate type hexamethylene diisocyanate, manufactured by Asahi Chemical Industries Co., Ltd.)
**Castor oil (glyceryl triricinoleate)
Solidified state:
○: solidified into gel-like form within 24 hours
X: not solidified
State after one day:
Good: no change
Bleed: allyl isothiocyanate solution oozed out
Rubber hardness: measured value using Asker rubber hardness tester, Type C

TABLE 3

| Allyl isothiocyanate | 80% by weight | | | | | | | | |
|---|---|---|---|---|---|---|---|---|---|
| Polyisocyanate % by wt., wt. ratio to polyol* | 17.91 (90) | 15.92 (80) | 13.93 (70) | 11.94 (60) | 9.95 (50) | 7.96 (40) | 5.97 (30) | 3.98 (20) | 1.99 (10) |
| Polyol. % by wt** wt. ratio to isocyanate | 1.99 (10) | 3.98 (20) | 5.97 (30) | 7.96 (40) | 9.95 (50) | 11.94 (60) | 13.93 (70) | 15.92 (80) | 17.91 (90) |
| Dibutyltin dilaurate | 0.1 | 0.1 | 0.1 | 0.1 | 0.1 | 0.1 | 0.1 | 0.1 | 0.1 |

TABLE 3-continued

| Allyl isothiocyanate | 80% by weight | | | | | | | | |
|---|---|---|---|---|---|---|---|---|---|
| Solidified state | ○ | ○ | ○ | ○ | ○ | ○ | ○ | X | X |
| State after one day | bleed | bleed | bleed | good | good | good | good | — | — |
| Rubber hardness | — | — | — | 15–17 | 16–18 | 7–8 | 0.1–1 | — | — |

*Duranate THA-100 (isocyanurate type hexamethylene diisocyanate, manufactured by Asahi Chemical Industries Co., Ltd.)
**Castor oil (glyceryl triricinoleate)
Solidified state:
○: solidified into gel-like form within 24 hours
X: not solidified
State after one day:
Good: no change
Bleed: allyl isothiocyanate solution oozed out
Rubber hardness: measured value using Asker rubber hardness tester, Type C As seen from the results in Tables 1 through 3, gelling occurs regardless of the weight ratio of polyisocyanate to polyol when the amount of allyl isothiocyanate is low. In contrast, as the amount of allyl isothiocyanate increases, gelling occurs only in cases where the weight ratio of polyisocyanate to polyol is about 1:1.

A gel-like resin molded article contained in a volatilization control container according to the present invention is provided with a container having an opening portion for controlling a volatilization rate of the allyl isothiocyanate. The opening portion preferably occupies a contact area between the gelled drug and air surrounding the container in a proportion of 0.01 to 50%, more preferably 0.05 to 30%, and most preferably 0.1 to 20%, as described above. When the proportion of the opening portion is smaller than the above range, the period of time of allyl isothiocyanate volatilization is increased, but the amount of the volatile drug released from the container is lowered, thereby making it difficult to impossible to obtain a desired effect, which is not desirable. On the other hand, when the proportion of the opening portion is larger than the above range, the period of time of allyl isothiocyanate volatilization is decreased, thereby making it unusable for various end use applications, which is not desirable.

According to another embodiment of the present invention, in the gel-like resin molded article contained in a volatilization control container the container is made of a thermoplastic resin film through which allyl isothiocyanate can permeate. The permeability of the thermoplastic film to allyl isothiocyanate preferably is within a range from 0.05 to 10 mg/cm$^2$ day, more preferably from 0.05 to 5 mg/cm$^2$ day, and most preferably from 0.1 to 3 mg/cm$^2$ day. When the permeability is less than the above range, the period of time of allyl isothiocyanate volatilization is increased, but the amount of the volatile drug released is lowered, thereby making it difficult to impossible to obtain a desired effect, which is not desirable. On the other hand, when the permeability is greater than the above range, the period of time of allyl isothiocyanate volatilization is shortened, thereby making it unusable to use for various end use applications, which is not desirable.

Examples of a thermoplastic resin film which can be used in the present invention include polyethylene, polypropylene, ethylene-vinyl acetate, polyethylene terephthalate, polyvinyl chloride, nylon, and polyacetal films. The thickness of the film is appropriately selected according to the permeability of the film to allyl isothiocyanate. In the present invention, films obtained by laminating the films and other packaging materials, such as nonwoven fabric, also can be used. By using a film in combination with other packaging materials, it is possible to reinforce the film and to print on the film, thus improving the appearance of the product.

In the present invention, when using a polyethylene film as the thermoplastic resin film, the film thickness preferably is in a range from 40 to 500 μm, and more preferably from 100 to 300 μm. When using a polypropylene film as the thermoplastic resin film, the thickness preferably is in a range from 15 to 200 μm, and more preferably from 30 to 100 μm.

In the present invention, the surface of the container can be further provided with an aluminum foil laminate as a gas-impermeable packaging material. Formation of such an aluminum foil suppresses volatilization of the volatile drug before use of a volatile gel-like packaging drug.

The gelled drug of the present invention preferably has a rubber strength in a range from 0.1 to 100, more preferably from 5 to 85, concretely. As used herein, the term "rubber strength" refers to a value measured by using an Asker rubber hardness tester, Type C. When the rubber strength is less than the above range, the molded article composition is not converted into a gel-like form, resulting in poor handling, which is not desirable. On the other hand, when the rubber strength is greater than the above range, the molded article composition becomes hard such that allyl isothiocyanate does not migrate from the interior of the molded article to the surface, and the volatility of allyl isothiocyanate is reduced, which also is not desirable.

A gel-like resin molded article contained in a volatilization control container can be used even if the gelled drug is in the form of bulk, sheet, film, particle, powder, or coating. By molding into various forms, it is possible to obtain a gel-like resin molded article contained in a volatilization control container in a form suited for different end use applications.

The gel-like resin molded article contained in a volatilization control container can be used as a repellent for noxious organisms because allyl isothiocyanate is used as a volatile active agent. Specific examples of the noxious organisms include cockroaches, weevils, termites, rats, moles, dogs, cats, deer, crow, bear, and pigeon.

In the gel-like resin molded article contained in a volatilization control container according to the present invention, a gelled drug containing allyl isothiocyanate as a volatile ingredient is contained in a container having an opening portion which occupies a contact area between the gelled drug and air in a proportion of 0.01% to 50%. Therefore, it is possible to control the volatilization rate according to a particular end use application, and to set the period of time for volatilization according to that end use.

In a gel-like resin molded article contained in a volatilization control container according to the present invention, a gelled drug containing allyl isothiocyanate is contained in a container comprising a thermoplastic resin film having a permeability to allyl isothiocyanate of 0.05 to 10 mg/cm$^2$ day. Therefore, it is possible to control the volatilization rate according to a particular end use application and to set the period of time for volatilization according to that end use.

DESCRIPTION OF THE PREFERRED EMBODIMENTS

Figure 1:
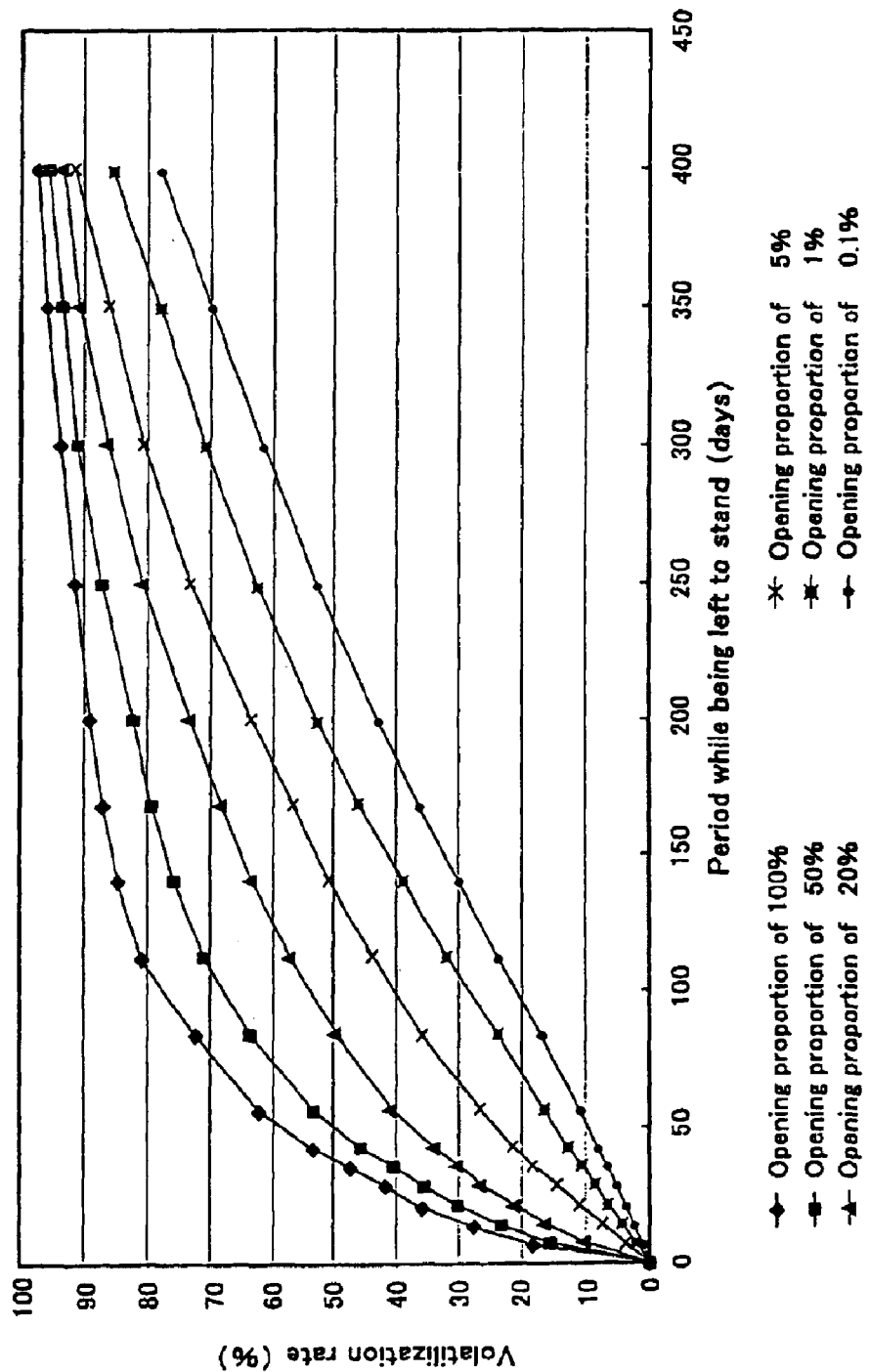
FIG. 1 is a graph showing the results of a relation between the opening proportion and the volatilization rate obtained by the measurement of a weight loss (% by weight) over a time period of 0 to 400 days.

The present invention will now be described by way of examples.

EXAMPLES 1 TO 5 AND COMPARATIVE EXAMPLE 1

In accordance with the formulation shown in Table 4, ingredients were mixed and dissolved in the order from the upper column of the same table. To the mixture, dibutyltin dilaurate was added and mixed to prepare a drug mixture (content of allyl isothiocyanate is 40% by weight). A container made of styrol (a cylindrical container having a diameter of 36 mm and a height of 35 mm, contact area with an air: 1017 mm$^2$) was filled with 20 g of the drug mixture, and then left to stand. Three hours after filling the container, the drug mixture converted into a gelled drug having no fluidity.

TABLE 4

|  | Amount (% by weight) |
|---|---|
| Castor oil (glyceryl triricinoleate) | 29.975 |
| Polylisocyanate* | 29.975 |
| Allyl isothiocyanate | 40.0 |

TABLE 4-continued

|  | Amount (% by weight) |
|---|---|
| Dibutyltin dilaurate (added in the form of a 10% ethyl acetate solution) | 0.1 |

*Duranate THA-100 (isocyanurate-type hexamethylene diisocyanate, manufactured by Asahi Chemical Industries Co., Ltd.).

The styrol container was provided with an opening portion which occupied a contact area between the gelled drug and air in a proportion of 50%, 20%, 5%, 1% or 0.1% (opening proportion) to obtain gel-like resin molded articles contained in volatilization control containers of Examples 1 to 5, respectively. For comparison, the styrol container was provided with an opening portion which occupies the same area as the contact area between the gelled drug and an air (opening proportion: 100%) to obtain gel-like resin molded article contained in a volatilization control container of Comparative Example 1.

EXAMPLES 6 TO 11 AND COMPARATIVE EXAMPLE 2

A drug mixture was prepared in accordance with the same formulation (Table 4) as in Examples 1 to 5. This drug mixture (20 g) was poured into an aluminum mold of 10 cm×5 cm in size, then allowed to stand. After standing for three hours, a gel-like sheet having a thickness of 0.4 cm with no fluidity was obtained. The sheet was cut into pieces of 4 cm×4 cm in size, placed in a thermoplastic resin bag of 6 cm×6 cm in size, then sealed airtight. Polyethylene bags of 40 μm and 100 μm in thickness (Examples 1 and 2), polypropylene bags of 40 μm and 100 μm in thickness (Examples 3 and 4), a PET (polyethylene terephthalate) bag of 15 μm in thickness (Example 5), and a nylon bag of 15 μm in thickness (Example 6) were used as the thermoplastic resin bag, respectively. In Comparative Example 2, a gel-like sheet was not put in the thermoplastic resin bag.

(Volatilization Rate Test)

With respect to the gel-like resin molded articles in the container of Examples 1 to 5 and Comparative Example 1, as well as Examples 6 to 11 and Comparative Example 2, the volatilization rate was determined by the measurement of a weight loss (% by weight). The results are shown in Table 5 and Table 6. Plots of data in Table 5 and Table 6 provide the graphs in FIG. 1 and FIG. 2.

TABLE 5

Opening Proportion and Volatilization Rate
Gelled Drug: amount of allyl isothiocyanate is 40% weight

| Period while being left to stand (days) | Opening proportion of 100% | Opening proportion of 50% | Opening proportion of 20% | Opening proportion of 5% | Opening proportion of 1% | Opening proportion of 0.1% |
|---|---|---|---|---|---|---|
| 0 | 0.0 | 0.0 | 0.0 | 0.0 | 0.0 | 0.0 |
| 7 | 18.2 | 15.5 | 10.1 | 4.1 | 2.3 | 1.3 |
| 14 | 27.6 | 23.4 | 16.2 | 7.7 | 4.4 | 2.6 |
| 21 | 35.6 | 30.2 | 21.3 | 11.2 | 6.7 | 3.9 |
| 28 | 41.6 | 35.3 | 26.4 | 14.8 | 9.0 | 5.3 |
| 35 | 47.5 | 40.4 | 30.3 | 18.6 | 10.7 | 6.8 |
| 42 | 53.3 | 45.3 | 34.0 | 21.5 | 12.8 | 8.3 |
| 56 | 6.23 | 53.0 | 40.8 | 26.8 | 16.7 | 10.9 |
| 84 | 72.3 | 63.6 | 49.6 | 35.9 | 23.9 | 16.8 |
| 112 | 80.7 | 71.0 | 57.3 | 43.8 | 31.8 | 23.8 |
| 140 | 84.5 | 75.8 | 63.6 | 50.7 | 38.8 | 29.9 |
| 168 | 86.8 | 79.4 | 68.4 | 56.7 | 45.6 | 36.2 |

TABLE 5-continued

Opening Proportion and Volatilization Rate
Gelled Drug: amount of allyl isothiocyanate is 40% weight

| Period while being left to stand (days) | Opening proportion of 100% | Opening proportion of 50% | Opening proportion of 20% | Opening proportion of 5% | Opening proportion of 1% | Opening proportion of 0.1% |
|---|---|---|---|---|---|---|
| 200 | 89.0 | 82.2 | 73.5 | 63.6 | 52.7 | 42.6 |
| 250 | 91.2 | 87.1 | 80.7 | 73.3 | 62.5 | 52.7 |
| 300 | 93.6 | 90.9 | 86.1 | 80.3 | 70.8 | 61.5 |
| 350 | 95.7 | 93.2 | 90.7 | 85.7 | 77.8 | 69.6 |
| 400 | 96.9 | 95.1 | 93.2 | 91.1 | 84.9 | 77.7 |

TABLE 6

Kinds and thickness of thermoplastic resin film and volatilization rate
Gelled drug: amount of allyl isothiocyanate is 40% by weight

| Period while being left to stand (days) | PE40 µm | PE100 µm | PP 40 µm | PP 100 µm | PET 15 µm | Nylon 15 µm | No packaging |
|---|---|---|---|---|---|---|---|
| 0 | 0.0 | 0.0 | 0.0 | 0.0 | 0.0 | 0.0 | 0.0 |
| 7 | 26.3 | 13.5 | 8.2 | 4.3 | 0.0 | 0.0 | 35.3 |
| 14 | 44.8 | 28.6 | 15.1 | 8.1 | 0.0 | 0.0 | 53.0 |
| 21 | 56.8 | 40.3 | 20.8 | 12.0 | 0.0 | 0.1 | 65.0 |
| 28 | 66.8 | 51.0 | 25.7 | 15.9 | 0.1 | 0.2 | 75.6 |
| 35 | 71.6 | 58.7 | 30.8 | 19.8 | 0.1 | 0.3 | 80.2 |
| 42 | 75.6 | 63.5 | 34.9 | 23.8 | 0.2 | 0.4 | 84.1 |
| 49 | 78.6 | 68.6 | 39.9 | 27.7 | 0.3 | 0.4 | 87.4 |
| 56 | 81.5 | 71.9 | 43.6 | 31.8 | 0.3 | 0.5 | 90.0 |
| 63 | 83.8 | 74.4 | 48.6 | 35.6 | 0.4 | 0.5 | 91.8 |
| 70 | 85.2 | 76.1 | 52.4 | 39.4 | 0.4 | 0.6 | 93.3 |
| 77 | 86.4 | 78.6 | 56.4 | 43.8 | 0.5 | 0.7 | 94.2 |
| 84 | 88.4 | 80.3 | 60.3 | 47.7 | 0.6 | 0.7 | 95.1 |
| 91 | 89.3 | 82.0 | 64.4 | 51.9 | 0.6 | 0.8 | 95.8 |
| 98 | 90.1 | 83.1 | 68.5 | 56.1 | 0.7 | 0.8 | 96.2 |
| 105 | 90.9 | 84.3 | 71.6 | 59.7 | 0.8 | 0.9 | 97.0 |
| 112 | 91.8 | 85.5 | 74.8 | 63.6 | 0.8 | 1.0 | 97.2 |
| 119 | 92.3 | 86.8 | 79.2 | 68.4 | 0.9 | 1.1 | 97.8 |
| 126 | 92.7 | 88.0 | 81.8 | 71.9 | 1.0 | 1.1 | 98.3 |
| 133 | 93.2 | 89.1 | 84.8 | 76.3 | 1.0 | 1.2 | 98.6 |
| 140 | 93.8 | 90.0 | 86.8 | 78.9 | 1.1 | 1.3 | 99.0 |

As seen from Table 5 and FIG. 1, an initial volatilization rate (gradient of the graph in FIG. 1) in the gel-like resin molded article of Comparative Example 1 is very large, and the volatilization rate decreases after a lapse of 30 to 40 days, thereby substantially shortening the volatilization time period. In contrast, the volatilization rate becomes uniform and the volatilization time period is shortened as the opening proportion decreases in the gel-like resin molded articles in the container of Examples 1 to 5.

Figure 2:
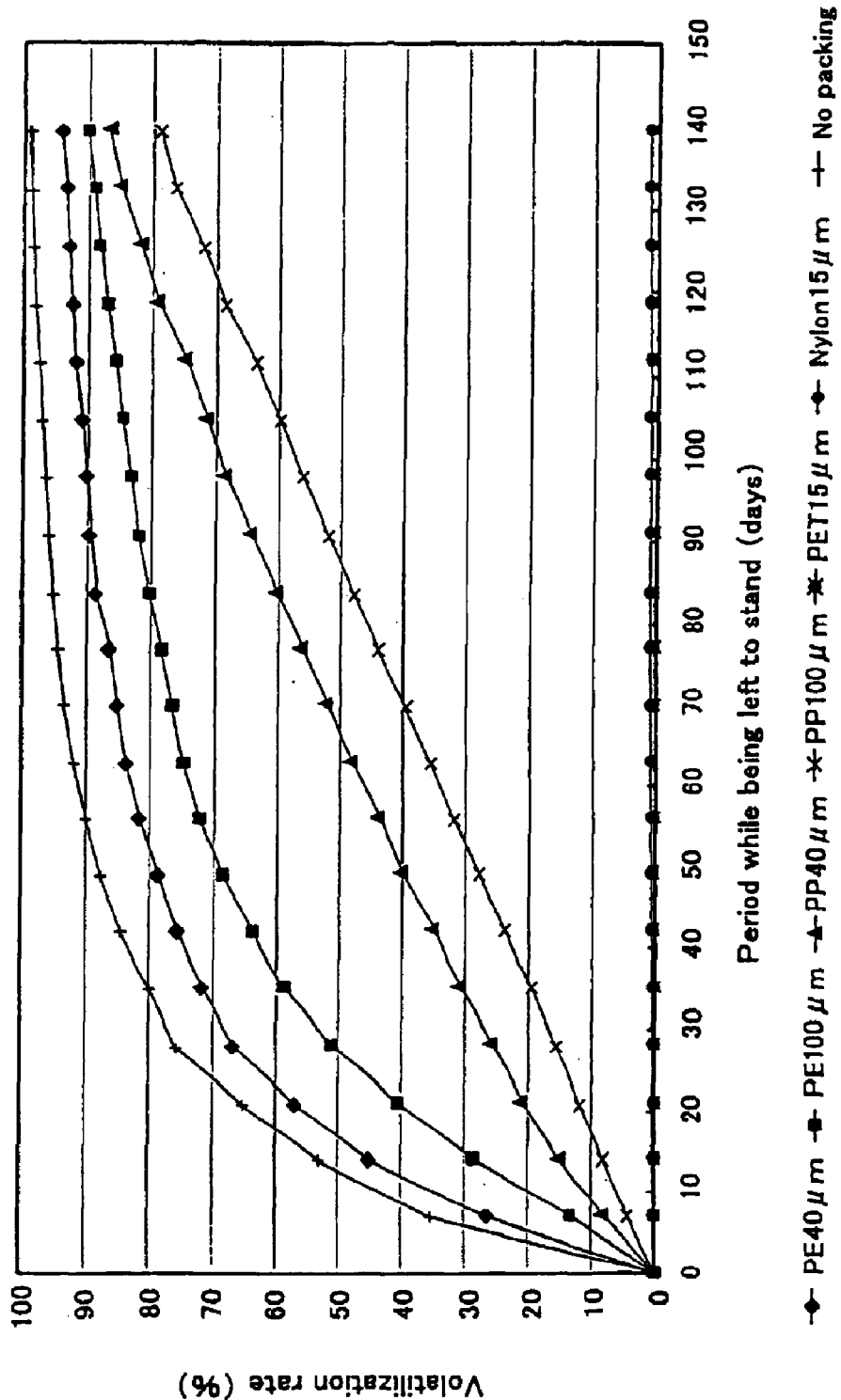
FIG. 2 is a graph showing the results of a relation between the type and thickness of a thermoplastic resin film and the volatilization rate obtained by the measurement of a weight loss (% by weight) over a period of 0 to 140 days.

As seen from Table 6 and FIG. 2, an initial volatilization rate (gradient of the graph in FIG. 2) in the gel-like resin molded article of Comparative Example 2 is very large and the volatilization rate decreases after a lapse of 30 to 40 days, thereby substantially shortening the volatilization time period. In contrast, the volatilization rate is properly controlled in Examples 6 to 9. It is also apparent that, in Examples 10 and 11, the volatilization rate is small, thereby making it difficult to achieve the desired concentration of allyl isothiocyanate gas. Accordingly, it is necessary to use a film having a thickness less than 15 µm in case of PET and nylon for some end use applications.

(Permeability Test for Allyl Isothiocyanate)

To examine the effects of the type and thickness of a thermoplastic film on the permeability of allyl isothiocyanate, 5 g of allyl isothiocyanate was charged into a thermoplastic resin bag 6 cm×6 cm in size, and weight loss was measured on a wire fabric to obtain a weight of allyl isothiocyanate permeated per 1 cm$^2$ day. The results are shown in Table 7. As seen from Table 7, the permeability of allyl isothiocyanate largely depends on the type of thermoplastic resin film. It is also apparent that the volatilization rate decreases as the thickness of the film increases. it is possible to select the type and thickness of the thermoplastic resin film for a particular end use application from the results of Table 7.

TABLE 7

Permeability test results of thermoplastic resin film

| Material of film | Thickness (µm) | Permeability (mg/cm$^2$ day) |
|---|---|---|
| Nylon | 15 | 0.050 |
|  | 30 | 0.004 |
| Polyethylene terephthalate | 15 | 0.012 |
|  | 30 | 0.008 |
| Polyethylene | 40 | 3.7 |
|  | 100 | 1.5 |
| Polypropylene | 40 | 0.35 |
|  | 100 | 0.1 |
| Acrylonitrile-butadiene-m ethyl acrylate copolymer | 30 | 0.01 |
| Vinyl chloride | 30 | 0.02 |

What is claimed is:

1. A resin molded article contained in a volatilization control container comprising: (a) a gelled drug comprising (i) allyl isothiocyanate and (ii) a resin base comprising a polyurethane resin, contained in (b) a container for controlling a volatilization rate of the allyl isothiocyanate, wherein the container comprises an opening portion, and the opening portion occupies a contact area between the gelled drug and air surrounding the container in a proportion of from 0.01 to 50%, and wherein the allyl isothiocynate is present in an amount of more than 20% by weight and not more than 85%, by weight, base on the total weight of said gelled drug.

2. The resin molded article contained in a volatilization control container according to claim 1 wherein the rubber hardness of the gelled drug is from 0.1 to 100.

3. The resin molded article contained in a volatilization control container according to claim 1 wherein the gelled drug has a sheet form.

4. A method of repelling noxious organisms comprising providing a gel-like resin molded article contained in a volatilization container of claim 1, and allowing the allyl isothiocyanate to be released from the container through the opening portion to air surrounding the container.

5. The method of claim 4 wherein the noxious organism is selected from the group consisting of cockroach, weevil, termite, rat, mole, dog, cat, deer, crow, bear, and pigeon.

6. A resin molded article contained in a volatilization control container comprising: (a) a gelled drug comprising (i) allyl isothiocyanate and (ii) a resin base comprising a polyurethane resin, contained in (b) a container for controlling a volatilization rate of the allyl isothiocyanate, wherein the container comprises a thermoplastic resin film through which the allyl isothiocyanate can permeate and the permeability of the thermoplastic resin film to the allyl isothiocyanate is from 0.05 to 10 mg/cm$^2$ day, and wherein the allyl isothiocyanate is present in an amount of more than 20% by weight and not more than 85%, by weight, based on the total weight of said gelled drug.

7. A method of repelling noxious organisms comprising providing a gel-like resin molded article contained in a volatilization container of claim 6 and allowing the allyl isothiocyanate to permeate from the thermoplastic resin film to air surrounding the container.

8. The method of claim 7 wherein the noxious organism is selected from the group consisting of cockroach, weevil, termite, rat, mole, dog, cat, deer, crow, bear, and pigeon.

9. The resin molded article contained in a volatilization control container of claim 6 wherein the thermoplastic resin film is selected from the group consisting of polyethylene, polypropylene, ethylene-vinyl acetate, polyethylene terephthalate, polyvinyl chloride, nylon, a polyacetal film, laminates thereof, and laminates of said films and a non-woven fabric.

10. The resin molded article contained in a volatilization control container according to claim 6 wherein the rubber hardness of the gelled drug is from 0.1 to 100.

11. The resin molded article contained in a volatilization control container according to claim 6 wherein the gelled drug has a form selected group the group consisting of bulk, sheet, film, particle, powder, and coating.

* * * * *

UNITED STATES PATENT AND TRADEMARK OFFICE
CERTIFICATE OF CORRECTION

PATENT NO.     : 6,867,232 B1
DATED          : March 15, 2005
INVENTOR(S)    : Hironori Kataoka et al.

It is certified that error appears in the above-identified patent and that said Letters Patent is hereby corrected as shown below:

Title page,
Item [73], Assignee, delete "Seiaku" and insert -- Sieyaku --.

Column 11,
Line 12, delete "base" and insert -- based --.

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,867,232 B1
DATED : March 15, 2005
INVENTOR(S) : Hironori Kataoka et al.

It is certified that error appears in the above-identified patent and that said Letters Patent is hereby corrected as shown below:

Column 12,
Line 28, delete "group the group" and insert -- from the group --.

Signed and Sealed this

Seventh Day of February, 2006

JON W. DUDAS
*Director of the United States Patent and Trademark Office*